United States Patent
Weiss (10) Patent No.: US 12,193,753 B2
(45) Date of Patent: *Jan. 14, 2025

(54) SYSTEM FOR STIMULATING RENAL NERVES

(71) Applicant: KONINKLIJKE PHILIPS N.V., Eindhoven (NL)

(72) Inventor: Steffen Weiss, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 98 days.

This patent is subject to a terminal disclaimer.

(21) Appl. No.: 18/094,928

(22) Filed: Jan. 9, 2023

(65) Prior Publication Data

US 2023/0157758 A1 May 25, 2023

Related U.S. Application Data

(63) Continuation of application No. 15/745,941, filed as application No. PCT/EP2016/066462 on Jul. 12, 2016, now Pat. No. 11,547,480.

(30) Foreign Application Priority Data

Jul. 21, 2015 (EP) .................................. 15177702

(51) Int. Cl.
*A61B 18/14* (2006.01)
*A61B 5/021* (2006.01)
(Continued)

(52) U.S. Cl.
CPC .............. *A61B 34/10* (2016.02); *A61B 5/021* (2013.01); *A61B 18/1492* (2013.01);
(Continued)

(58) Field of Classification Search
CPC ...... A61B 34/10; A61B 5/021; A61N 1/36007
See application file for complete search history.

(56) References Cited

U.S. PATENT DOCUMENTS

| 8,852,163 B2 | 10/2014 | Deem |
| 2003/0216792 A1 | 11/2003 | Levin |

(Continued)

FOREIGN PATENT DOCUMENTS

| EP | 2460486 A1 | 6/2012 |
| WO | 2007103879 A2 | 9/2007 |

(Continued)

OTHER PUBLICATIONS

Tsioufis, Drug-Resistant Hypertensive Patients responding to Multielectrode renal Denervation Exhibit Improved Heart Rate Dynamics and Reduced Arrhythmia Burden, Journal of Human Hypertension, vol. 28, pp. 587-593, 2014.

(Continued)

*Primary Examiner* — Linda C Dvorak
*Assistant Examiner* — Ryan T Clark (57) ABSTRACT

A system is provided for stimulating renal nerves. The system includes an interstitial device to provide stimulation and denervation of the renal nerves from outside the renal artery. The interstitial device extends through non-vascular tissue and into a periarterial space. The system also includes a control unit in communication with the interstitial device, configured to: obtain, from a sensor, first information pertaining to a blood pressure or heart rate; stimulate, using one or more electrodes of the interstitial device, renal sympathetic nerves associated with the renal artery; and obtain, from the sensor, second information pertaining to the blood pressure or heart rate of the subject. Based on a difference between the first information and the second information, the control unit determines whether the subject is suitable for a sympathetic denervation procedure and causes the (Continued)

interstitial device to perform the sympathetic denervation procedure if the subject is suitable.

20 Claims, 3 Drawing Sheets

(51) Int. Cl.
| | | |
|---|---|---|
| *A61B 34/10* | (2016.01) | |
| *A61N 1/05* | (2006.01) | |
| *A61N 1/36* | (2006.01) | |
| *G16H 40/63* | (2018.01) | |
| *A61B 18/00* | (2006.01) | |

(52) U.S. Cl.
CPC ....... *A61N 1/0502* (2013.01); *A61N 1/36007* (2013.01); *A61N 1/36017* (2013.01); *G16H 40/63* (2018.01); *A61B 2018/00434* (2013.01); *A61B 2018/00839* (2013.01); *A61B 2505/05* (2013.01)

(56) References Cited

U.S. PATENT DOCUMENTS

| | | | |
|---|---|---|---|
| 2006/0041277 | A1 | 2/2006 | Deem |
| 2010/0222851 | A1* | 9/2010 | Deem ................ A61N 1/36139 607/44 |
| 2011/0306851 | A1 | 12/2011 | Wang |
| 2013/0158508 | A1 | 6/2013 | Consigny |
| 2014/0012133 | A1 | 1/2014 | Sverdlik |
| 2014/0194866 | A1 | 7/2014 | Wang |
| 2014/0276124 | A1 | 9/2014 | Cholette |
| 2015/0289929 | A1* | 10/2015 | Toth .................. A61B 18/1492 606/41 |
| 2019/0175903 | A1 | 6/2019 | Zarins |

FOREIGN PATENT DOCUMENTS

| | | |
|---|---|---|
| WO | 2011046879 A1 | 4/2011 |
| WO | 2013181137 A1 | 12/2013 |
| WO | 2014029355 A1 | 2/2014 |
| WO | 2014070999 A1 | 5/2014 |

OTHER PUBLICATIONS

Krum, H. et al "Catheter-based Renal Sympathetic Denervation for Resistant Hypertension: A Multicenter safety and proof-of-principle cohort study", The Lancet, vol. 373, pp. 1275-1281, 2009.

Smithwick, R.H. et al "Splanchnicectomy for essential hypertension; results in 1,266 cases", J Am Med Assoc. 1953;152:1501-4.

Fischell, T.A. et al, "Ethanol-mediated perivascular renal sympathetic denervation: preclinical validation of safety and efficacy in a porcine model", Eurointervention, 2013;vol. 9: 140-147.

Streitparth, F. et al MR-guided periarterial ethanol injection for renal sympathetic denervation: a feasibility study in pigs, Cardiovascularand Interventional Radiology, vol. 36, No. 3, pp. 791-796, 2013.

Chinushi, Masaomi et al "Blood Pressure and Autonomic Responses to Electrical Stimulation of the Renal Arterial Nerves Before and After Ablation of the Renal Artery" Renal Denervation, Hypertension 2013, vol. 61, pp. 450-456.

Harris, S.H. "Renal sympathectomy: its scope and limitations", Proceedings of the Roayl Society of Medicine, vol. 1497, 1935.

Lloyd-Jones, D. et al "Heart disease and stroke statistics—2010 update: a report from the American Heart Association" Circulation 2010, 121:e46-e215.

Wolf-Maier, K. et al Hypertension treatment and control in five European countries, Canada, and the United States. Hypertension 43:10-17, 2003.

Ricke J, et al. "Renal Sympathetic Denervation by CT-Guided Ethanol Injection", Cardiovascular Intervention Radiology, 2016.

* cited by examiner

SYSTEM FOR STIMULATING RENAL NERVES

CROSS REFERENCE TO RELATED APPLICATIONS

This application claims the priority benefit under 35 U.S.C. § 119(e) of U.S. patent application Ser. No. 15/745,941 filed Jan. 18, 2018, which claims priority to International Patent Application No. PCT/EP2016/066462, filed Jul. 12, 2016, which claims priority to EP Application No. 15177702.6, filed Jul. 21, 2015, each of which is hereby incorporated by reference in their entirety as though fully set forth herein.

FIELD OF THE INVENTION

The invention relates to a system and a method for stimulating renal nerves of a renal artery of a subject. The invention further relates to a computer program for controlling the system and to a needle device for stimulating the renal nerves. The invention also relates to a use of the needle device for carrying out the method for stimulating the renal nerves.

BACKGROUND OF THE INVENTION

The article "Catheter-based renal sympathetic denervation for resistant hypertension: a multicenter safety and proof-of-principle cohort study" by H. Krum et al., The Lancet, volume 373, pages 1275 to 1281 (2009) discloses a renal sympathetic denervation (RDN) procedure for treating hypertension, wherein the RDN procedure is carried out by using transvascular radiofrequency (RF) ablation.

The RDN procedure has the disadvantage that only about 20 percent of the patients, who undergo the RDN procedure, respond with a significant decrease in blood pressure. Thus, many patients are treated by using the transvascular RF ablation procedure without significantly improving the hypertension problem.

SUMMARY OF THE INVENTION

It is an object of the present invention to provide a system and a method for stimulating renal nerves of a renal artery of a subject, a computer program for controlling the system for stimulating the renal nerves, a needle device for stimulating the renal nerves and a use of the needle device for carrying out the method for stimulating the renal nerves, which allow for a reduction of the likelihood that a subject undergoes an RDN procedure without having a significant effect on blood pressure.

In a first aspect of the present invention a system for stimulating renal nerves of a renal artery of a subject is presented, wherein the system comprises:
a stimulation device for stimulating the renal nerves,
a measuring unit for measuring the blood pressure and/or the heart rate of the subject at at least two times, wherein at least one of these times is during or after the stimulation of the renal nerves, and
a subject suitability determination unit for determining whether the subject is suitable for an RDN procedure based on the measured blood pressure and/or measured heart rate.

Since based on the measurement of the blood pressure and/or the heart rate at at least two times, wherein at least one of these times is during or after the stimulation of the renal nerves, it is determined whether the subject is suitable for an RDN procedure, a preselection of subjects can be provided, wherein the RDN procedure may be applied only to the preselected subjects. This can lead to a significant decrease of the likelihood that a subject undergoes an RDN procedure without having a marked effect on blood pressure.

Preferentially the stimulation device comprises at least two electrodes for stimulating the renal nerves, wherein the at least two electrodes may include a ring electrode. Moreover, the stimulation device is preferentially adapted to stimulate the renal nerves in a pulsed mode. The stimulation device may be adapted to stimulate the renal nerves for, for instance, one minute. Furthermore, the stimulation device may be adapted to stimulate the renal nerves with electrical pulses having a pulse duration being smaller than 5 ms. The frequency of the provision of the electrical pulses may be smaller than 20 Hz, and the amplitude of the current of the electrical pulses may be smaller than 15 mA.

It is preferred that the subject suitability determination unit is adapted to determine a blood pressure change parameter being indicative of a change in blood pressure based on the measured blood pressure and/or a heart rate change parameter being indicative of a change in heart rate based on the measured heart rate, and to determine that the subject is suitable for the RDN procedure based on the blood pressure change parameter and/or the heart rate change parameter, respectively. It is further preferred that the subject suitability determination unit is adapted to determine that the subject is suitable for the RDN procedure, if the blood pressure change parameter indicates an increase of the blood pressure and/or the heart rate change parameter indicates an increase of the heart rate. In particular, the subject suitability determination unit is adapted to determine that the subject is suitable for the RDN procedure, if the blood pressure change parameter indicates that the blood pressure has increased by at least 20 percent and/or if the heart rate change parameter indicates that the heart rate has increased by at least 10 percent. These percentage values preferentially refer to a comparison of a reference value measured before or at the beginning of the stimulation process and a value measured during or after the stimulation process. By determining that the subject is suitable for the RDN procedure in this way, the preselection of subjects, who will respond with a significant decrease in blood pressure on the RDN procedure, can be further improved.

The subject suitability determination unit can be adapted to determine a) the blood pressure change parameter depending on the slope of the measured blood pressure and/or on a difference between blood pressure values measured at different times and/or a ratio between blood pressure values measured at different times and/or b) the heart rate change parameter depending on the slope of the measured heart rate and/or on a difference between heart rate values measured at different times and/or a ratio between heart rate values measured at different times. In particular, a time-dependent blood pressure change parameter can be determined depending on a) a blood pressure value measured at a reference time, which might be at the start of or before stimulating the renal nerves, and b) a blood pressure value measured at further times during and/or after the stimulation process. Correspondingly, a time-dependent heart rate change parameter can be determined depending on a) a heart rate value measured at a reference time, which might be at the start of or before stimulating the renal nerves, and b) a heart rate value measured at further times during and/or after the stimulation process. The determined time-dependent blood pressure change parameter and the time-dependent heart rate change parameter can be used for measuring changes in blood pressure and heart rate caused by the stimulation process.

The stimulation device comprises preferentially an interstitial device. Thus, the stimulation device is preferentially adapted to interstitially stimulate the renal nerves. In particular, the stimulation device may include an interstitial needle device. The needle device is preferentially a device which comprises or can make use of a needle-like element like a mandrin with a sharpened tip for facilitating an introduction into the subject. If the stimulation device is adapted for interstitial stimulation, the procedure for stimulating the renal nerves may be simplified, because it is not necessary to access the renal artery through the vascular tree. It is just required to traverse muscle and fat tissue. The stimulation procedure can then also be performed in subjects with stenosed, atherosclerotic or natively small or strongly curved arteries. It is therefore possible to apply the stimulation procedure to more subjects in a simplified way.

The system preferentially comprises an RDN device for performing an RDN procedure. Moreover, the system may comprise a control unit for controlling the RDN device, wherein the control unit may be adapted to control the RDN device such that the RDN procedure is performed only, if the subject suitability determination unit has determined that the subject is suitable for an RDN procedure. This ensures that the RDN procedure is only performed, if the subject will really respond with a marked decrease in blood pressure on the RDN procedure.

The RDN device preferentially comprises an interstitial device, especially an interstitial needle device, for performing the RDN procedure interstitially. This allows performing the RDN procedure without requiring an advancement of, for instance, an element of the RDN device through the vessel tree to the renal artery. The RDN procedure can therefore also be performed in subjects with stenosed, atherosclerotic or natively small or strongly curved arteries. It is just required to traverse muscle and fat tissue. Thus, also the RDN procedure can be carried out with more subjects in a simpler way.

The RDN device is preferentially adapted to inject a neurolytic fluid into the periarterial space of the renal artery for performing the RDN procedure. The neurolytic fluid is preferentially ethanol. However, it can also be another neurolytic fluid like glycerol. Injecting a neurolytic fluid leads to circumferential denervation, even if it is delivered to a single point only. This is caused by the fact that the neurolytic fluid generally spreads around the entire artery.

The RDN device is preferentially integrated with the stimulation device. For instance, the stimulation device and the RDN device may be integrated by using a same component for stimulation and for the RDN procedure. This same component may comprise at least two electrodes for stimulating the renal nerves and an injection unit for injecting the neurolytic fluid into the periarterial space of the renal artery. This allows testing whether the subject is suitable for the RDN procedure and performing the RDN procedure, if it has been determined that the subject is suitable, by using a single component to be introduced into the subject. This can lead to a simplified overall procedure including the suitability determination and the RDN procedure. The component is preferentially adapted to stimulate the renal nerves and to perform the RND procedure interstitially, i.e. not by introducing the component via, for instance, the femoral artery into the renal artery. In particular, the component may be a needle device for being introduced into the body through muscle and fat tissue, in order to reach the renal artery.

It is preferred that the stimulation device is adapted to stimulate the renal nerves while performing the RDN procedure, wherein the measuring unit is adapted to measure the blood pressure and/or the heart rate at at least two times, wherein at least one of these times is during or after the stimulation of the renal nerves, which is performed while performing the RDN procedure. It is also preferred that the system comprises a termination determination unit for determining when the RDN procedure should be terminated based on the blood pressure and/or heart rate measured at at least two times, wherein at least one of these times is during or after the stimulation of the renal nerves, which is performed while performing the RDN procedure. Moreover, it is preferred that the system comprises a control unit for controlling the RDN device such that the RDN procedure is stopped, if the termination determination unit has determined that RDN procedure should be stopped. This can ensure that the RDN procedure is performed such that the blood pressure of the subject is significantly decreased, without performing the RDN procedure unnecessarily longer. The RDN procedure is therefore only performed as long as it really has an effect on the blood pressure.

The RDN procedure can be performed continuously or stepwise, i.e. the RDN procedure may include, for instance, continuously injecting the neurolytic fluid or injecting the neurolytic fluid in several steps, wherein in between two injection steps, which may also be regarded as being denervation steps, no neurolytic fluid is injected. Thus, the RDN procedure may cover denervation steps and intermediate non-denervation periods. Also the stimulation of the renal nerves may be performed continuously or stepwise. In an embodiment the RDN procedure and the stimulation of the renal nerves may both be performed continuously, wherein the RDN procedure and the stimulation may start at the same start time. At this start time also a reference blood pressure and/or a reference heart rate may be measured. During the RDN procedure and while stimulating the renal nerves the blood pressure and/or the heart rate may be further measured at different times, especially continuously, and a corresponding time-dependent blood pressure change parameter and/or a corresponding time-dependent heart rate change parameter, respectively, may be determined based on the reference blood pressure and/or the reference heart rate and the further measured blood pressure and/or heart rate, respectively. Based on this time-dependent blood pressure change parameter and/or this time-dependent heart rate change parameter the termination determination unit can determine when the RDN procedure should be terminated.

If in an embodiment the RDN procedure is performed continuously and the stimulation is performed stepwise, at the beginning of the RDN procedure or before the beginning of the RDN procedure a reference blood pressure and/or a reference heart rate may be measured. While continuously performing the RDN procedure, the renal nerves may be stimulated in several stimulation steps, wherein during and/or after each stimulation step the blood pressure and/or the heart rate may be measured at least one time. These blood pressure and/or heart rate measurements may be used together with the reference heart rate and/or the reference blood pressure, respectively, in order to determine for each stimulation step at least one blood pressure change parameter and/or heart rate change parameter, respectively. Based on these blood pressure change parameters and/or heart rate change parameters determined for different stimulation steps the termination determination unit can determine when the RDN procedure should be terminated.

Moreover, in an embodiment the RDN procedure may be performed stepwise and the stimulation may be performed continuously. In this case the stimulation may start before or at the beginning of the first RDN procedure step. A reference blood pressure and/or a reference heart rate may be measured at the beginning of the first RDN procedure step or before. The blood pressure and/or the heart rate may be further measured at different times during and/or in between steps of the RDN procedure, wherein a time-dependent blood pressure change parameter and/or a time-dependent heart rate change parameter, respectively, may be determined based on these measurements and the reference blood pressure and/or the reference heart rate, respectively. The termination determination unit can then determine when the RDN procedure should be terminated based on the time-dependent blood pressure change parameter and/or the time-dependent heart rate change parameter.

In a further embodiment the RDN procedure may be performed stepwise and the stimulation of the renal nerves may also be performed stepwise. If the RDN procedure is performed stepwise, the RDN procedure covers denervation steps and intermediate non-denervation periods. If in this case the stimulation of the renal nerves is performed while performing the RND procedure, the stimulation of the renal nerves may be performed while carrying out the denervation steps and/or in the intermediate non-denervation periods. In an embodiment the RDN procedure steps and the stimulation steps may be performed alternatingly, wherein at the beginning of a stimulation step a reference blood pressure and/or a reference heart rate may be measured and wherein during and/or at the end of the stimulation step one or several further blood pressure and/or heart rate measurements may be performed. Based on these measurements and the reference blood pressure and/or the reference heart rate, respectively, a blood pressure change parameter and/or a heart rate change parameter, respectively, may be determined and used by the termination determination unit for determining whether a next RDN procedure step should be performed or not, i.e. whether the RDN procedure should be terminated. In further embodiments the RDN procedure and the stimulation of the renal nerves may be combined in another way for monitoring the response of the blood pressure and/or the heart rate to the stimulation of the renal nerves while performing the RDN procedure, wherein the RDN procedure may be stopped, if the blood pressure and/or the heart rate do not respond anymore to the stimulation.

In a further aspect of the present invention a needle device for stimulating renal nerves of a renal artery of a subject is presented, wherein the needle device is adapted to stimulate the renal nerves and to perform an RDN procedure interstitially. The needle device can be used together with a measuring unit for measuring the blood pressure and/or the heart rate of the subject, in order to determine whether the subject is suitable for an RDN procedure. In particular, the needle device can be used for stimulating the renal nerves, wherein the blood pressure and/or the heart rate can be measured at at least two times, wherein at least one of these times is during or after the stimulation of the renal nerves and wherein based on the measured blood pressure and/or heart rate it can be determined whether the subject is suitable for the RDN procedure. If the subject is suitable for the RDN procedure, the same needle device can be used for performing the RDN procedure. The needle device therefore allows performing the RDN procedure only, if the subject will respond with a marked decrease in blood pressure, i.e. the needle device allows for a significant decrease of the likelihood that a subject undergoes an RDN procedure without having a marked effect on blood pressure.

In a further aspect of the present invention a method for stimulating renal nerves of a renal artery of a subject is presented, wherein the method comprises:
stimulating the renal nerves by a stimulation device,
measuring the blood pressure and/or the heart rate of the subject at at least two times by a measuring unit, wherein at least one of these times is during or after the stimulation of the renal nerves,
determining whether the subject is suitable for an RDN procedure based on the measured blood pressure and/or the measured heart rate.

In a further aspect of the present invention a use of the needle device as defined in claim 12 for carrying out the method as defined in claim 13 is presented.

Moreover, in an aspect of the present invention a computer program for controlling a system for stimulating renal nerves of a renal artery of a subject as defined in claim 1 is presented, wherein the computer program comprises program code means for causing the system to carry out the method for stimulating renal nerves of a renal artery of a subject as defined in claim 13, when the computer program is run on the system.

It shall be understood that the system of claim 1, the needle device of claim 12, the method of claim 13, the use of the needle device of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
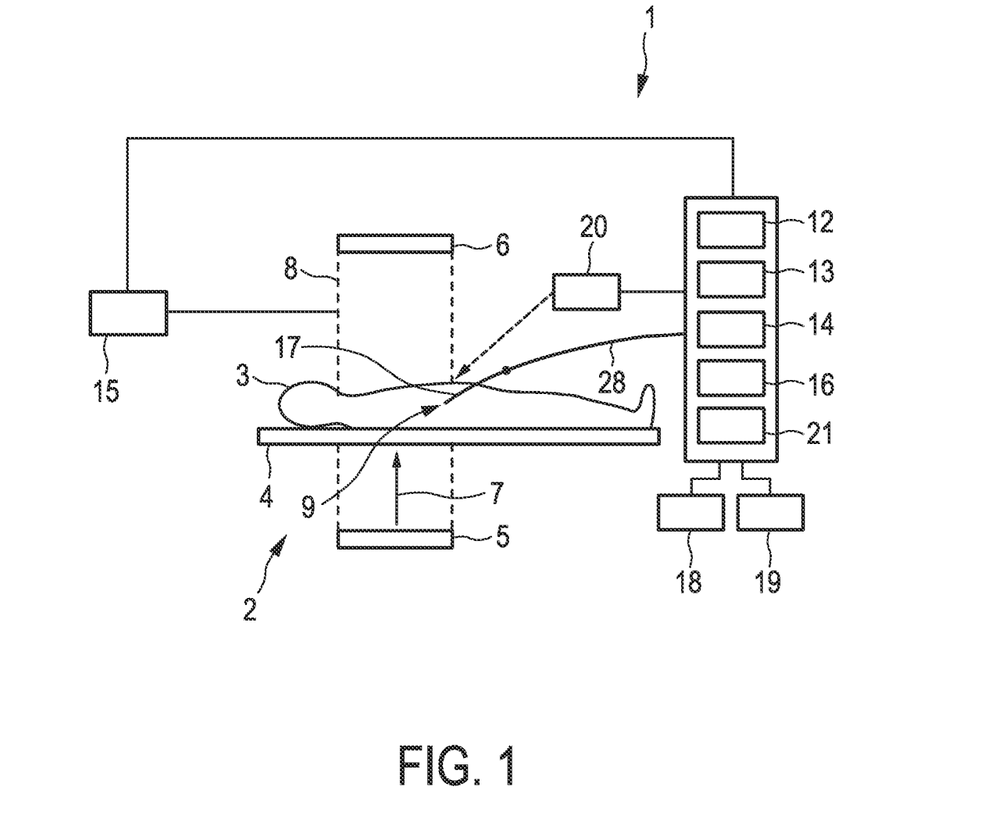
FIG. 1 shows schematically and exemplarily an embodiment of a system for stimulating renal nerves of a renal artery of a subject.

FIG. 1 shows schematically and exemplarily an embodiment of a system 1 for stimulating renal nerves of renal artery of a subject 3 who is arranged on a support means like a table 4. The system 1 comprises an imaging device 2 for generating an image showing the inside of the subject 3, especially showing a renal artery of the subject 3. In the example shown, the subject is a person but such procedure could also be performed on an animal.

In this embodiment the imaging device 2 is a computed tomography imaging device comprising a radiation source 5 for generating radiation 7 traversing the subject 3 and a detector 6 for detecting the radiation 7 after having traversed the subject 3. The radiation source 5 and the detector 6 are mounted on a rotatable gantry 8 such that the radiation 7 can traverse the subject 3 in different directions. The detector 6 generates projection data values based on the detected radiation and provides the projection data values to a reconstruction and control unit 15. The reconstruction and control unit 15 is adapted to reconstruct a computed tomography image of the subject 3, which may be shown on a display 19. Moreover, the reconstructing and control unit 15 is adapted to control the rotation of the gantry 8, the radiation source 5 and the detector 6. In another embodiment another imaging device can be used for generating an image of the inside of the subject 3, especially of a renal artery of the subject 3, like a magnetic resonance imaging system or an ultrasound imaging system.

The system 1 further comprises an interstitial needle device 17 which is adapted to be introduced through muscle and fat tissue into the subject 3 such that the tip 9 of the needle device 17 is adjacent to a renal artery of the subject 3. For planning the introduction of the needle device 17 a computed tomography image generated by the imaging device 2 is used.

The needle device 17 comprises at its tip 9 two electrodes for stimulating renal nerves of a renal artery of the subject 3. The two electrodes for stimulation the renal nerves are coupled via a connection element 28 to an electrical power source 12 that is configured to provide current pulses. Thus, by using the electrical power source 12, the connection element 28 and the electrodes at the tip 9 of the needle device 17 the renal nerves of the renal artery of the subject 3 can be stimulated by using current pulses. The electrical power source 12, the connection element 28 and the needle device 17 can therefore be regarded as forming a stimulation device. The current pulses are preferentially provided with a frequency being smaller than 20 Hz and with an amplitude being smaller than 15 mA. The duration of a pulse may be about 5 ms.

The needle device 17 further comprises a means for performing an RDN procedure. In this embodiment this means is an injection means for injecting neurolytic fluid into the periarterial space of the renal artery. In particular, the needle device 17 comprises a lumen, which is connected to a corresponding lumen within the connection element 28, wherein the lumen within the connection element 28 is connected to a neurolytic fluid providing unit 13 for providing the neurolytic fluid. The neurolytic fluid providing unit 13 preferentially comprises a reservoir of the neurolytic fluid and a pump for pumping the neurolytic fluid through the lumina in the connection element 28 and the needle device 17 to the tip 9 of the needle device, wherein at the tip 9 of the needle device the neurolytic fluid is injected into the periarterial space of the renal artery. The neurolytic fluid providing unit 13, the connection element 28 and the needle device 17 can therefore be regarded as forming an RDN device.

Figure 2:
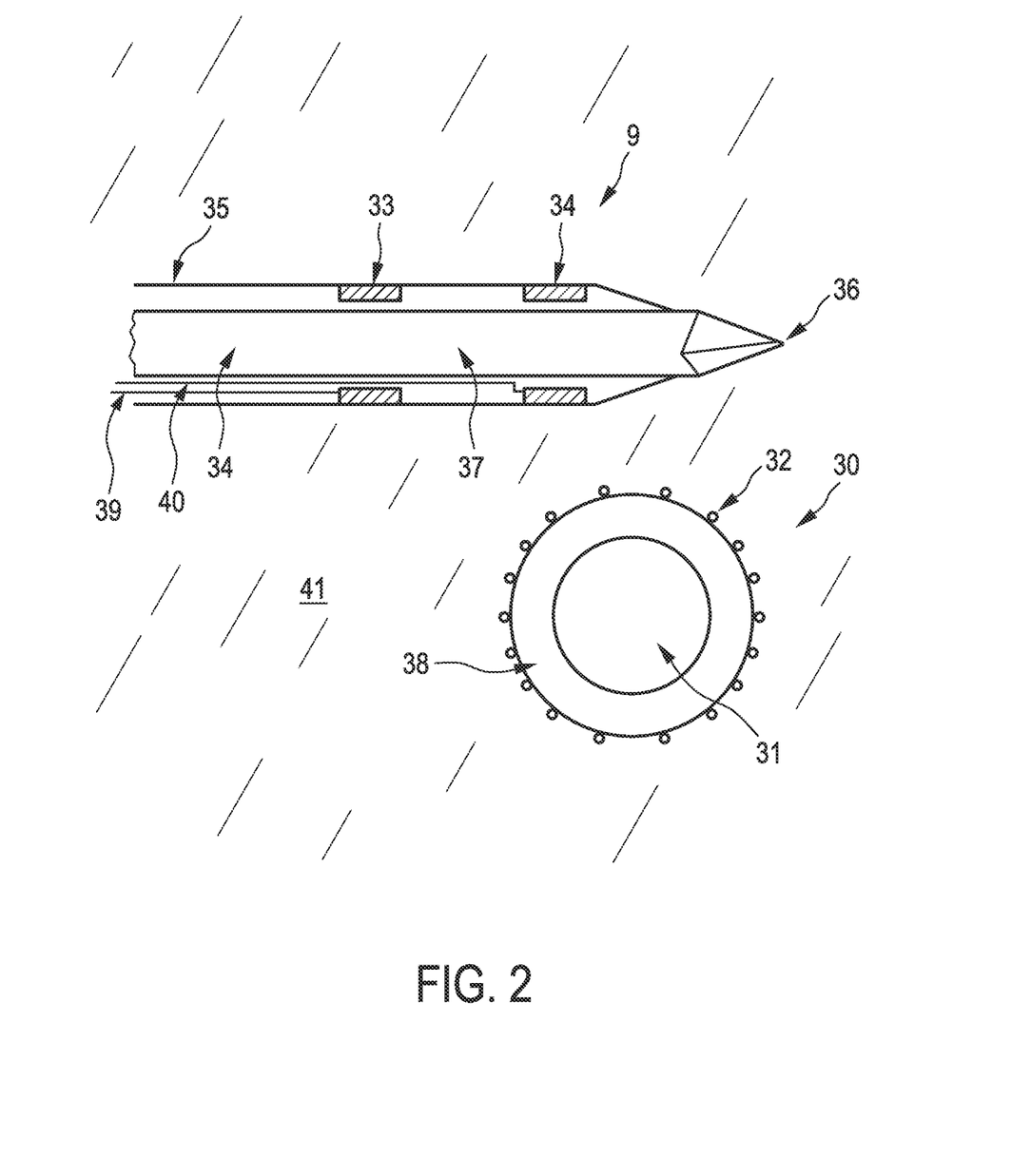
FIG. 2 shows schematically and exemplarily a tip of a needle device of the system shown in FIG. 1 and a renal artery.

FIG. 2 shows schematically and exemplarily the tip 9 of the needle device 17 in more detail. In this embodiment the two electrodes for stimulating the renal nerves 32 are ring electrodes 33, 34 embedded in a wall 35 enclosing the lumen 34 of the needle device 17. The ring electrodes 33, 34 are connected to the electrical power source 12 via electrical connections, especially electrical wires, 39, 40. For inserting the needle device 17, especially the tip 9 of the needle device 17, a supporting structure 37 like a mandrin with a sharp end 36 is introduced into the lumen 34 of the needle device 17. The sharp end 36 of the supporting structure 37 allows for an insertion of the tip 9 of the needle device 17 through muscle tissue and fat tissue such that the tip 9 reaches the periarterial space of the renal artery 30. The insertion of the tip 9 of the needle device 17 may be performed manually by a user like a physician under image guidance, i.e. the imaging device 2 may be used to generate images at different points in time for showing the respective current position of the tip 9 of the needle device 17 within the subject 3. In addition or alternatively, other known techniques may be used for monitoring the position of the tip 9 of the needle device 17 within the subject 3, which may use an electromagnetic localization system, a localization system being based on optical shape sensing et cetera. In an embodiment the tip 9 of the needle device 17 may also be automatically inserted into the subject 3 based on images generated by using the imaging device 2 and/or location information informing about the current position of the tip 9 of the needle device 17, which may be provided by a localization system.

After the tip 9 of the needle device 17 has been inserted into the subject 3 and reached the periarterial space of the renal artery 30, the supporting structure 37 can be removed from the lumen 34 of the needle device 17, in order to use the lumen 34 for injecting the neurolytic fluid into the periarterial space of the renal artery 30.

The renal artery 30 comprises an inner lumen 31 for carrying the blood, a wall 38 and outer renal nerves 32. The renal artery 30 is surrounded by connective tissue 41 in which the renal nerves 32 are embedded. The electric field generated by the ring electrodes 33, 34 reaches the renal nerves 32 of the renal artery 30 through the connective tissue 41, even if there is no direct contact between the ring electrodes 33, 34 and the renal nerves 30.

Thus, in this embodiment a stimulation device and an RDN device form an integrated device with a single interstitial needle device 17. In other embodiments the RDN device and the stimulation device can be separate devices. Moreover, the stimulation device and/or the RDN device may not be adapted to perform interstitial procedures, i.e. at least one of these devices may be adapted to forward a stimulation element or an RDN element, respectively, to a renal artery of a subject through the vessel tree. Furthermore, the RDN device can be adapted to perform the RDN procedure in another way, i.e. not by using a neurolytic fluid. For instance, an RF ablation technique can be used for performing the RDN procedure.

The system 1 further comprises a measuring unit 20 for measuring the blood pressure and the heart rate of the subject 3 while stimulating the renal nerves. The measuring unit 20 can use known techniques for measuring the blood pressure and the heart rate. For instance, the measuring unit 20 may include a pressure cuff with automated air pump to measure both blood pressure and heart rate, wherein the pressure cuff may be worn at the upper arm or the wrist. The measuring unit 20 may also include a simple pulse-oximeter at the fingertip for measuring the heart rate.

The system further comprises a subject suitability determination unit 14 for determining whether the subject 3 is suitable for an RDN procedure based on the blood pressure and the heart rate measured while stimulating the renal nerves.

In this embodiment the subject suitability determination unit 14 is adapted to determine a blood pressure change parameter being indicative of a change in blood pressure based on the measured blood pressure and a heart rate change parameter being indicative of a change in heart rate based on the measured heart rate and to determine that the subject 3 is suitable for the RDN procedure based on the blood pressure change parameter and the heart rate change parameter. Preferentially the subject suitability determination unit 14 is adapted to determine that the subject is suitable for the RDN procedure, if the blood pressure change parameter and the heart rate change parameter indicate that the blood pressure and the heart rate increase when stimulating the renal nerves. In particular, the subject suitability determination unit 14 is adapted to determine that the subject is suitable for the RDN procedure, if the blood pressure change parameter indicates that the blood pressure has increased by at least 20 percent and if the heart rate change parameter indicates that the heart rate has increased by at least 10 percent while stimulating the renal nerves.

The subject suitability determination unit 14 can be adapted to determine a) the blood pressure change parameter depending on the slope of the measured blood pressure and/or on a difference between blood pressure values measured at different times and/or a ratio between blood pressure values measured at different times and b) the heart rate change parameter depending on the slope of the measured heart rate and/or on a difference between heart rate values measured at different times and/or a ratio between heart rate values measured at different times. In particular, a time-dependent blood pressure change parameter can be determined depending on a) a blood pressure value measured at a reference time, which might be at the start of or before stimulating the renal nerves, and b) a blood pressure value measured at further times during and/or after the stimulation process. Correspondingly, a time-dependent heart rate change parameter can be determined depending on a) a heart rate value measured at a reference time, which might be at the start of or before stimulating the renal nerves, and b) a heart rate value measured at further times during and/or after the stimulation process. The determined time-dependent blood pressure change parameter and the time-dependent heart rate change parameter can be used for monitoring changes in blood pressure and heart rate caused by the stimulation process.

The system 1 further comprises a control unit 16 for controlling the RDN device, especially the neurolytic fluid providing unit 13, such that the RDN procedure is performed only, if the subject suitability determination unit 14 has determined that the subject 3 is suitable for an RDN procedure. This ensures that the RDN procedure is not unnecessarily carried out.

The stimulation device is adapted to stimulate the renal nerves also while performing the RDN procedure, wherein the measuring unit 20 is adapted to measure the blood pressure and the heart rate at at least two times, wherein at least one of these times is during or after the stimulation of the renal nerves, which is carried out while performing the RDN procedure. The system 1 further comprises a termination determination unit 21 for determining when the RDN procedure should be terminated based on the blood pressure and the heart rate measured at at least two times, wherein at least one of these times is during or after the stimulation of the renal nerves, which is carried out while performing the RDN procedure. In particular, the termination determination unit 21 is adapted to determine that the RDN procedure should be stopped, if the blood pressure and the heart rate do not respond to the stimulation anymore, i.e. if an increase of the blood pressure and an increase of the heart rate cannot be observed while stimulating the renal nerves. The termination determination unit 21 hence determines the end point of the RDN procedure. The control unit 16 is adapted to control the RDN device, especially the neurolytic providing unit 13, such that the RDN procedure is stopped, if the termination determination unit 21 has determined the end point of the RDN procedure.

The system 1 further comprises an input unit 18 for allowing the user to input parameters like control parameters into the system 1. For instance, the user can input a parameter for indicating that the stimulation of the renal nerves should be started or should be stopped or that the RDN procedure should be started or should be stopped.

In the following an embodiment of a method for stimulating renal nerves of a renal artery of a subject and of performing an RDN procedure will be exemplarily described with reference to a flowchart shown in FIG. 2.

Figure 3:
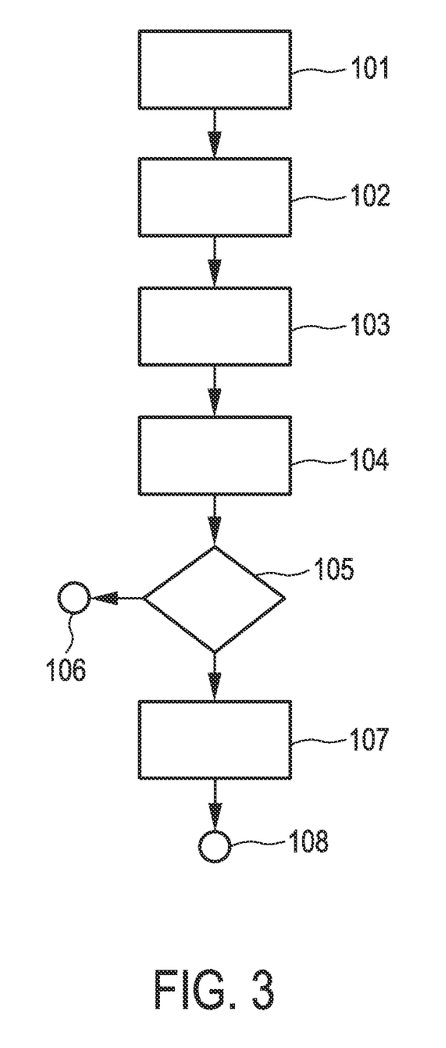
FIG. 3 shows a flowchart exemplarily illustrating an embodiment of a method for stimulating renal nerves of a renal artery of a subject.

In step 101 a preprocedural three-dimensional image of the subject 3 is generated, which shows at least one renal artery of the subject 3, by using the imaging device 2. In step 102 an introduction path for introducing the needle device 17 is planned based on the generated three-dimensional image such that the tip 9 of the needle device 17 will reach a renal artery shown in the three-dimensional image. If the three-dimensional image shows several renal arteries, a renal artery may be selected, which is most easily accessible, wherein criteria for this selection process might be the degree of straightness and the diameter of the renal arteries. A further criterion for selecting a most easily accessible renal artery might be whether the respective artery is relatively isolated such that an introduction path can easily be found, which avoids veins. A further criterion might be whether the respective renal artery can be easily accessed without interfering with the rib cage.

In step 103 the needle device 17 is inserted to the periarterial space of the selected renal artery along the planned introduction path. This insertion procedure is preferentially performed under realtime image guidance, wherein at different points in time, particularly continuously, images are generated by the imaging device 2, which show the needle device 17 while being moved along the planned introduction path. In step 104 the renal nerves of the selected renal artery, i.e. the renal afferent nerves, are stimulated by using the needle device 17 and the electrical power source 12. In particular, the renal nerves are stimulated for 1 min by using current pulses having a pulse duration of about 5 ms and an amplitude being smaller than 15 mA. The pulse frequency is preferentially smaller than 20 Hz. While stimulating the renal nerves the blood pressure and the heart rate are measured in step 104 by using the measuring unit 20.

In step 105 it is determined whether the subject is suitable for an RDN procedure based on the blood pressure and the heart rate measured in step 104 while stimulating the renal nerves. In particular, it is determined whether the measured blood pressure and heart rate increase on stimulation, wherein, if this is not the case, it is determined that the subject is not suitable for the RDN procedure and the method stops in step 106. Otherwise, in step 107 the RDN procedure is performed.

While performing the RDN procedure in step 107, the renal nerves are stimulated and the blood pressure and the heart rate are measured, wherein based on the measured blood pressure and heart rate it is determined whether the RDN procedure should be stopped. In particular, in step 107 an increase of the blood pressure and the heart rate due to the stimulation is continuously measured, wherein, if the blood pressure and the heart rate do not increase due to the stimulation anymore, it is determined that the end point is reached for the selected renal artery and the RDN procedure stops in step 108. Steps 102 to 108 may then be repeated with a further renal artery, especially with the contralateral renal artery.

The main problem of known RDN procedures is that many treated patients do not respond with a marked decrease in blood pressure on the RDN procedure. One important reason is that hypertension is often caused by many more factors than high sympathetic nerve activity alone. It is therefore important to select only those patients for the RDN procedure, which really respond with a marked decrease in blood pressure. The above described system for stimulating renal nerves of a renal artery of a subject allows for such a selection by monitoring the blood pressure and the heart rate of the respective subject while stimulating the renal nerves. Another important problem in known RDN procedures is the lack of a clinical end point during the RDN procedure. It is generally not known at which point in time the denervation is successfully completed. This lack of information often leads to a too long RDN procedure or to an insufficient RDN procedure, wherein the RDN procedure has been stopped too early. Hence, the completeness and long term effectiveness of the treatment cannot be determined during the RDN procedure. End points as used in cardiac ablation procedures as conduction block or signal voltage decrease cannot be used, because the renal nerve activity is too small for intra-procedural detection. The above described system solves this problem by stimulating the renal nerves during the RDN procedure, wherein the response in the blood pressure and in the heart rate on the stimulation is monitored. If the stimulation of the renal nerves does not lead to a response in the blood pressure and the heart rate anymore, the end point has been detected and the RDN procedure can be stopped.

The effort for a transvascular access is generally relatively high such that in above described embodiments a needle device is used for carrying out an interstitial RDN procedure by ethanol injection that includes stimulation electrodes that can be used to select those patients who do respond to RDN therapy. If an interstitial ethanol injection RDN procedure is performed, the vein and artery can remain intact. Moreover, the entire procedure for determining whether a person is suitable for an RDN procedure can be very fast. For instance, the planning time for planning the introduction path may be about 5 min, the time for inserting the needle device along the introduction path may be about 2 min, the renal nerves may then be stimulated for about 2 min, and the response to the stimulation, i.e. the possible increase of the blood pressure and the heart rate, may be measured for about 12 min after the start of stimulation, resulting in an overall procedure time of about 20 min. After it has been determined that the person is suitable for the RDN procedure, the RDN procedure, i.e. the denervation of the renal nerves, can be carried out, especially by injecting neurolytic fluid.

Although in above described embodiments computed tomography is used for guiding the insertion of the needle device into the subject, in other embodiments other imaging techniques can be used for guiding the introduction process. For instance, a magnetic resonance imaging device or an ultrasound imaging device can be used for this guidance purpose.

Although in above described embodiments the suitability of the respective subject for the RDN procedure is determined based on the heart rate and the blood pressure, in other embodiments the suitability of the respective subject for the RDN procedure may be determined based only on the measured heart rate or only on the measured blood pressure. Correspondingly, also the end point of the RDN procedure may be determined only based on the measured heart rate or only based on the measured blood pressure, which is measured at at least two times, wherein at least one of these times is during or after the stimulation of the renal nerves, wherein in this case the renal nerves are stimulated while performing the RDN procedure.

Although in above described embodiments ring electrodes are used for stimulating the renal nerves, in other embodiments other electrodes like point electrodes may be used for stimulating the renal nerves.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination whether a subject is suitable for an RND procedure, determining when an RND procedure should be terminated, et cetera performed by one or several units or devices can be performed by any other number of units or devices. These procedures and/or the control of the above described system for stimulating renal nerves of a renal artery of a subject in accordance with the above described method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a system for stimulating renal nerves of a renal artery of a subject. The system comprises a stimulation device for stimulating the renal nerves, a measuring unit for measuring the blood pressure and/or the heart rate of the subject at at least two times, wherein at least one of these times is during or after the stimulation of the renal nerves, and a subject suitability determination unit for determining whether the subject is suitable for an RDN procedure based on the measured blood pressure and/or the measured heart rate. The invention allows therefore for a preselection of subjects which are suitable for a renal sympathetic denervation procedure.

The invention claimed is:

1. A system for stimulating renal nerves of a renal artery of a subject, the system comprising:
   an interstitial device configured to provide interstitial stimulation and renal sympathetic denervation of the renal nerves from a location outside the renal artery, wherein the interstitial device is configured to reach the location outside the renal artery without being advanced inside a blood vessel; and
   a control unit in communication with the interstitial device, the control unit configured to:
   obtain, from a sensor, first information pertaining to a blood pressure or heart rate of the subject;
   cause the interstitial device to provide the interstitial stimulation to the renal nerves;
   obtain, from the sensor after the interstitial stimulation of the renal nerves, second information pertaining to the blood pressure or heart rate;

determine, based on a difference between the first information and the second information, whether the subject is suitable for the renal sympathetic denervation; and cause the interstitial device to provide the renal sympathetic denervation to the renal nerves if the subject is suitable for the renal sympathetic denervation.

2. The system of claim 1, wherein the control unit is further configured to:

obtain, from the sensor, during the renal sympathetic denervation, obtain third information pertaining to the blood pressure or heart rate of the subject; and determine, based on a difference between the second information and the third information, whether to stop the renal sympathetic denervation.

3. The system of claim 1, wherein the control unit is further configured to:

obtain, from the sensor, after the renal sympathetic denervation, fourth information pertaining to the blood pressure or heart rate of the subject; and determine, based on a difference between the second information and the fourth information, whether to repeat the renal sympathetic denervation.

4. The system of claim 1, wherein the interstitial device is configured to perform the renal sympathetic denervation by stimulation with electrical energy, RF ablation, or injection of a neurolytic fluid.

5. The system of claim 4, wherein the interstitial device is configured to perform the renal sympathetic denervation by the injection of the neurolytic fluid, and wherein the neurolytic fluid comprises ethanol or glycerol.

6. The system of claim 1, wherein the the interstitial device comprises at least one ring electrode.

7. The system of claim 1, wherein the interstitial device is configured to provide the interstitial stimulation by delivering pulses of electrical energy to the renal nerves.

8. The system of claim 7, wherein the interstitial device is configured to deliver the pulses of electrical energy with a pulse duration of less than 5 milliseconds.

9. The system of claim 7, wherein the interstitial device is configured to deliver the pulses of electrical energy with a frequency of is less than 20 Hz.

10. The system of claim 7, wherein the interstitial device is configured to deliver the pulses of electrical energy with an amplitude smaller than 15 milliamperes.

11. The system of claim 1, wherein the interstitial device is configured to deliver the pulses of electrical energy for less than 2 minutes.

12. The system of claim 1, wherein the first information is a first blood pressure measurement and the second information is a second blood pressure measurement.

13. The system of claim 1, wherein the first information is a first heart rate measurement and the second information is a second heart rate measurement.

14. The system of claim 1, wherein the control unit is further configured to:

obtain the first information from the sensor in less than 12 minutes; and obtain the second information from the sensor in less than 12 minutes.

15. A method for stimulating renal nerves of a renal artery of a subject, the method comprising:

providing an interstitial device configured to perform interstitial stimulation and renal sympathetic denervation of the renal nerves from a location outside the renal artery, wherein the interstitial device is configured to reach the location outside the renal artery without being advanced inside a blood vessel; and with a control unit in communication with the interstitial device:

obtaining, from a sensor, first information pertaining to a blood pressure or heart rate of the subject;

causing the interstitial device to provide the interstitial stimulation to the renal nerves;

obtaining, from the sensor after the interstitial stimulation of the renal nerves, second information pertaining to the blood pressure or heart rate of the subject;

determining, based on a difference between the first information and the second information, whether the subject is suitable for the renal sympathetic denervation; and causing the interstitial device to provide the renal sympathetic denervation to the renal nerves if the subject is suitable for the renal sympathetic denervation.

16. The method of claim 15, further comprising, with the control unit:

obtaining, from the sensor, during the renal sympathetic denervation, obtain third information pertaining to the blood pressure or heart rate of the subject; and determining, based on a difference between the second information and the third information, whether to stop the renal sympathetic denervation.

17. The method of claim 15, further comprising, with the control unit:

obtaining, from the sensor, after the renal sympathetic denervation, fourth information pertaining to the blood pressure or heart rate of the subject; and determining, based on a difference between the second information and the fourth information, whether to the renal sympathetic denervation.

18. The method of claim 15, wherein the causing the interstitial device to perform the renal sympathetic denervation if the subject is suitable for the renal sympathetic denervation comprises performing the renal sympathetic denervation by stimulation with electrical energy, RF ablation, or injection of a neurolytic fluid.

19. The method of claim 18, wherein the performing the renal sympathetic denervation includes the injection of the neurolytic fluid, and wherein the neurolytic fluid comprises ethanol or glycerol.

20. The method of claim 15, wherein the interstitial device comprises at least one ring electrode, and wherein the interstitial stimulation comprises stimulating the renal nerves for less than two minutes by delivering pulses of electrical energy with a pulse duration of less than 5 milliseconds, a frequency of less than 20 Hz, and an amplitude smaller than 15 milliamperes.

\* \* \* \* \*